United States Patent
Ballevre et al.

(10) Patent No.: US 7,910,144 B2
(45) Date of Patent: Mar. 22, 2011

(54) PET FOOD COMPOSITION FOR TREATING HELICOBACTER SPECIES IN PETS

(75) Inventors: Oliver Ballevre, Lausanne (CH); Iréne Corthesy-Theulaz, Epalinges (CH); Adolphe MarcYves Enslen, Lausanne (CH)

(73) Assignee: Nestec S.A., Vevey (CH)

( * ) Notice: Subject to any disclaimer, the term of this patent is extended or adjusted under 35 U.S.C. 154(b) by 836 days.

(21) Appl. No.: 10/195,909

(22) Filed: Jul. 15, 2002

(65) Prior Publication Data

US 2003/0049240 A1 Mar. 13, 2003

Related U.S. Application Data

(63) Continuation of application No. PCT/EP00/13374, filed on Dec. 28, 2000.

(30) Foreign Application Priority Data

Jan. 18, 2000 (EP) .................................. 00200179

(51) Int. Cl.
*A23L 1/00* (2006.01)
*C12N 1/00* (2006.01)
*A01N 63/02* (2006.01)

(52) U.S. Cl. .... 426/61; 435/243; 435/252.1; 435/252.9; 426/805; 426/71; 424/93.1; 424/93.45

(58) Field of Classification Search .................. 424/492, 424/93.45; 435/243, 252.1, 252.5, 252.9, 435/253.6; 426/61
See application file for complete search history.

(56) References Cited

U.S. PATENT DOCUMENTS

| | | | | |
|---|---|---|---|---|
| 5,578,302 | A | 11/1996 | Brassart et al. | 424/93.45 |
| 5,834,002 | A | 11/1998 | Athanikar | 424/440 |
| 5,968,569 | A * | 10/1999 | Cavadini et al. | 426/61 |
| 6,156,355 | A * | 12/2000 | Shields et al. | 426/74 |

OTHER PUBLICATIONS

Dictionary definitions of "infection" and "metabolite." http://www.dictionary.com, accessed Jan. 27, 2005. 2 pages.*
Gordon JB. How B vitamins work. http://www.howstuffworks.com/vitamin-b.htm accessed Oct. 10, 2005. 6 pages.*
Nabisco Inc. OREO sandwich cookies product detail. http://www.nabiscoworld.com/./Brands/ProductInformation.aspx?BrandKey=oreo&Site=1&Product=4400000820 accessed Oct. 10, 2005. 1 page.*
Rosenberg J. The history of the OREO cookie. http://history1900s.about.com/ library/weekly/aa083101a.htm accessed Oct. 10, 2005. 2 pages.*
Dalton S. 1997. Overweight and weight management. Aspen Publishers, Inc., Gaithersburg, MD. p. 274.*
Coconnier MH et al. 1998. Antagonistic activity against Helicobacter infection in vitro and in vivo by the human Lactobacillus acidophilus strain LB. Appl Environ Microbiol 64: 4573-4580.*
Media Formulations—Dulbecco's Modified Eagle Medium. Invitrogen, Inc. <url://www.invitrogen.com/content.cfm?pageId=95&fuseaction=MediaForm.dsp_mediaForm&productId=51>. Retrieved from the Internet on Dec. 3, 2007. 3 pages.*
Gomes AMP et al. 1999. Bifidobacterium spp. and Lactobacillus acidophilus: biological, biochemical, technological and therapeutical properties relevant for use as probiotics. Trends Food Sci Tech 10: 139-157.*

* cited by examiner

Primary Examiner — L E Barnhart
(74) Attorney, Agent, or Firm — K&L Gates LLP

(57) ABSTRACT

The present disclosure provides compositions intended for the prophylaxis or the treatment of disorders related to GHLO infections in pets, the compositions are prepared using at least one strain of lactic bacteria and/or one of its metabolites or a medium fermented by at least one lactic bacteria that has been isolated and selected for its ability to display a strong anti-*Helicobacter* bactericidal activity in vitro.

2 Claims, No Drawings

PET FOOD COMPOSITION FOR TREATING HELICOBACTER SPECIES IN PETS

CROSS-REFERENCE TO RELATED APPLICATION

This application is a continuation of the U.S. national stage designation of International application PCT/EP00/13374 filed Dec. 28, 2000, the entire content of which is expressly incorporated herein by reference thereto.

TECHNICAL FIELD

The present invention relates to the use of an isolated strain of lactic bacteria for the preparation of a food composition intended for the prophylaxis or treatment of disorders related to infection by *Helicobacter*-like-organisms in pets. The invention also relates to pet food composition prepared thereof.

BACKGROUND ART

It is known that in humans, infection with the pathogenic *Helicobacter pylori* can cause gastritis, and lead to ulcerative disease and gastric tumors. The methods of treatment are numerous. It has been shown previously in U.S. Pat. No. 5,578,302 (Nestlé) that lactic acid bacteria are able to inhibit *Helicobacter pylori* both in vitro and in vivo.

Domestic carnivores such as dogs and cats are virtually all infected with other species of gastric *Helicobacters*. Most of them cannot be cultured in vitro, but morphologically resemble *H. heilmannii*. *H. felis* was also isolated from cat gastric mucosa and, recently, two new *Helicobacter* species, named *H. bizzozeronii* and *H. salomonis*, were isolated from dogs. However, the only morphological analysis does not allow one to discriminate between these *Helicobacter* species and are grouped under the denomination of "Gastric *Helicobacter* like organisms" (GHLOs).

GHLOs colonize the antrum and/or the corpus of pets while *H. pylori* colonization mainly takes place in the corpus. Colonizing GHLOs organisms are located deep in the gastric fundic glands and sometimes are found actually within gastric parietal cell canaliculi as well as in the pits and gastric mucus, compared to *H. pylori* which is known as a non-invasive bacteria. (Dunn et al, 1997: "Hp are located in the mucus adherent to the surface epithelium and are often found deep within the crypts" ... )

The contamination of cat and dog stomach by *Helicobacter* species is considered as an important risk factor to develop mild to moderate gastritis. The inflammation observed is usually less severe than the one occurring in human infected with *H. pylori*. More severe lesions such as stomach ulcers, lymphomas and cancers can be observed but the pathogenicity of GHLOs is far from being clarified.

Nevertheless, controlling the infection by GHLOs in cat and dog to a low level is recognized by most veterinarians as a benefit. Since it is not a fully recognized disease requiring drug therapy, a food product containing an active ingredient capable of minimizing GHLO infection in cats and dogs is mostly required. The present invention now addresses this need.

SUMMARY OF THE INVENTION

The present invention relates to the use of at least one strain of lactic acid bacteria and/or its metabolites or a medium fermented by at least one lactic acid bacteria that have been isolated and selected for its ability to display a strong anti-*Helicobacter* bactericidal activity in vitro, for the preparation of a composition intended for the prophylaxis or the treatment of disorders related to GHLO infections in pets.

In a preferred embodiment, a metabolite produced by the isolated strain or a fermented medium by such lactic acid bacteria, or a subfraction of cultured medium fermented by the isolated strain of lactic acid bacteria is used.

The lactic acid bacteria strain may be selected from the group consisting of *Lactobacillus johnsonii*, *Lactobacillus reuterii*, *Lactobacillus paracasei*, *Lactobacillus animalis*, *Lactobacillus ruminis*, *Lactobacillus acidophilus*, *Lactobacillus rahmnosus*, *Lactobacillus fermentum*, *Bifidobacterium* sp., *Bifidobacterium lactis*, and *Bifidobacterium animalis*.

In a preferred embodiment the lactic bacteria strain is selected from the group consisting of *Lactobacillus johnsonii* NCC 533 (CNCM-I 1225), *Lactobacillus fermentum* NCC 2581 (CNCM I-2448), *Lactobacillus fermentum* NCC 2592 (CNCM I-2450), *Lactobacillus fermentum* NCC 2613 (CNCM I-2452), *Lactobacillus paracasei* NCC 2461 (CNCM-I 2116), *Lactobacillus animalis* NCC 2603 (CNCM I-2451), *Lactobacillus rahmnosus* NCC 2583 (CNCM I-2449), *Lactobacillus acidophilus* NCC 2628 (CNCM I-2453), *Bifidobacterium* sp. NCC 2627, *Bifidobacterium* sp. NCC 2657, *Bifidobacterium lactis* (ATCC 27536).

The invention also relates to a method for the treatment or for the prophylaxis of disorders related to GHLO infections in pets. This method comprises administering to a pet a composition containing at least one strain of lactic acid bacteria and/or its metabolites or a medium fermented by at least one lactic acid bacteria that have been isolated and selected for its ability to display a strong anti-*Helicobacter* bactericidal activity in vitro.

The invention also provides a pet food composition containing at least an isolated strain of lactic acid bacteria and/or one of its metabolites or a medium fermented by at least one lactic bacteria having the above traits, associated with an ingestible support or a pharmaceutical matrix.

This pet food composition is able to decrease GHLO infections in cats and dogs so that the GHLO load and the urease activity are reduced to a grade of at least 0.5 in the fundus and at least 0.5 in the antrum.

The effect of the composition on chronic gastritis was also evaluated by cytological examination of biopsy on thin sections. It can induce a regression of chronic fundic gastritis, with an average regression of the grade of gastric inflammation (graded from 0 to 3) of at least 0.5.

In another embodiment of the invention, this pet food composition may induce a significant reduction of breath odors which are correlated with the level of infection by GHLOs.

DETAILED DESCRIPTION OF THE PREFERRED EMBODIMENTS

Within the following description, the term "GHLOs" defines the "Gastric *Helicobacter*-like-organisms". Species of *Helicobacter* such as *Helicobacter felis*, *H. heilmannii*, *H. bizzozeroni* and *H. salomonis*, for example, which have been shown to colonize the gastric mucosa in pets, are grouped under this denomination.

Moreover, included within the term "GHLOs disorders" are all disorders which may affect directly the gastro intestinal tract of pets, but also secondary disorders such as bad breath symptoms, for example.

Finally, "NCC" designates Nestlé Culture Collection (Nestlé Research Center, Vers-chez-les-Blanc, Lausanne, Switzerland).

It has been found that at least one lactic acid bacteria strain and/or one of its metabolites or a medium fermented by at least one strain of lactic acid bacteria that is able to display a strong anti-*Helicobacter* bactericidal activity in vitro, should be used for the preparation of a composition intended for the prophylaxis or the treatment of disorders related to GHLOs infection in pets.

These strains have been selected among lactic bacteria strains with regard to their technological and physiological parameters and in particular for their good growth characteristics, i.e., at least $5\times10^8$ bacteria/ml, preferably $10^6$-$10^{10}$ bact/ml, most preferably $10^9$-$10^{10}$ bact/ml, as well as to their ability to display a strong anti-*Helicobacter* bactericidal activity in vitro.

In a preferred embodiment the lactic acid bacteria strain may be selected from the group consisting of *Lactobacillus johnsonii, Lactobacillus reuterii, Lactobacillus paracasei, Lactobacillus animalis, Lactobacillus ruminis, Lactobacillus acidophilus, Lactobacillus rahmnosus, Lactobacillus fermentum, Bifidobacterium* sp., *Bifidobacterium lactis*, and *Bifidobacterium animalis*.

The lactic bacteria strain is preferably selected from the group consisting of *Lactobacillus johnsonii* NCC 533 (CNCM-I 1225), *Lactobacillus fermentum* NCC 2581 (CNCM I-2448), *Lactobacillus fermentum* NCC 2592 (CNCM I-2450), *Lactobacillus fermentum* NCC 2613 (CNCM I-2452), *Lactobacillus paracasei* NCC 2461 (CNCM-I 2116), *Lactobacillus animalis* NCC 2603 (CNCM I-2451), *Lactobacillus rahmnosus* NCC 2583 (CNCM I-2449), *Lactobacillus acidophilus* NCC 2628 (CNCM I-2453), *Bifidobacterium* sp. NCC 2627, *Bifidobacterium* sp. NCC 2657, *Bifidobacterium lactis* (ATCC 27536).

Among the various strains selected in accordance with the present invention, the following strains were deposited by way of example under the Budapest Treaty at the Collection Nationale de Cultures de Microorganismes (CNCM), Institut Pasteur, 28 rue du Docteur Roux, 75724 Paris Cedex 15, France, *Lactobacillus johnsonii* (NCC 533) on the 30.06.92 under the reference CNCM I-1225, *Lactobacillus paracasei* (NCC 2461) on the 12.01.99 under the reference CNCM I-2116 and *Lactobacillus fermentum* NCC 2581, NCC 2592, NCC 2613, *Lactobacillus animalis* NCC 2603, *Lactobacillus rahmnosus* NCC 2583, *Lactobacillus acidophilus* NCC 2628 on 19.04.00 under the references (CNCM I-2448), (CNCM I-2450), (CNCM I-2452) (CNCM I-2451), (CNCM I-2449), (CNCM I-2453), respectively. The strain of *Bifidobacterium lactis* (ATCC27536) is provided by Hansen (Chr. Hansen A/S, 10-12 Boege Alle, P.O. Box 407, DK-2970 Hoersholm, Danemark).

Biochemical Characterization of the Selected Strains

*Lactobacillus johnsonii* CNCM I-1225
Gram positive microorganism, non-motile, non-sporing
Fairly short and thick rodlets
Microaérophilic microorganism with homofermentative metabolism, production of L (+) and D (−) lactic acid.
Catalase (−), production of $CO_2$ (−), hydrolysis of arginine (−)
Fermentation of sugars: Amygdaline (+), arabinose (−), cellobiose (+), esculine (+), fructose (+), galactose (−), glucose (+), lactose (+), maltose (+/−), mannitol (−), mannose (+), melibiose (−), raffinose (−), ribose (−), salicine (+), sucrose (+), tréhalose (+).

*Lactobacillus paracasei* CNCM I-2116
Gram positive
Catalase negative,
NH3 form arginine negative,
CO2 production negative production of L(+) lactic acid,
growth in the presence of bile salts in a concentration of up to about 0.4%.

The isolated strain of lactic bacteria and/or its fermented medium of culture may be used for the preparation of compositions intended for improving pet health, and particularly for the prevention or treatment of disorders related to GHLO infections in pets.

They can also be used in other disorders related to GHLOs such as bad breath odors. In fact, the presence of GHLOs in cat and dog stomach may have a clear influence on breath odors by producing large quantity of ammonia from urea. This ammonia can appear in breath after eructation. Bad breath could be also related to the presence of GHLOs in the stomach by the production of sulfide volatiles compounds. Preferably, the metabolites produced by these strains are intended to reduce bad breath odors and freshen the pet's breath.

A subfraction of cultured medium fermented by the isolated strain of lactic acid bacteria may also be used.

The lactic acid bacteria strain according to the invention, may be used in its viable or inactivated form.

In a preferred embodiment the lactic bacteria strain is used in the presence of its fermented growth medium. The medium can be either sterilized alone or with a food, extruded or spray-dried, chilled or shelf stable.

The lactic acid bacteria or the equivalent fermentation medium may be used so that the amount available for the pet may correspond to about $10^3$-$10^{14}$ cfu per day. This amount depends on the animal weight, and it is preferably of about $10^9$-$10^{12}$ cfu/day for dogs and $10^7$-$10^{11}$ cfu/day for cats.

In another embodiment, the invention relates to a method for the treatment or for the prophylaxis of disorders related to GHLO infections in pets, which comprises administering to a pet a composition containing at least one strain of lactic acid bacteria and/or a medium fermented by at least one lactic acid bacteria having the above traits. The amount available for the pet may correspond to about $10^3$-$10^{14}$ cfu per day, and it is preferably of about $10^9$-$10^{12}$ cfu/day for dogs and $10^7$-$10^{11}$ cfu/day for cats.

The present invention also relates to a pet food composition containing at least an isolated strain of lactic acid bacteria and/or its metabolites or fermented growth medium, said lactic bacteria having the above traits, associated with an ingestible support or a pharmaceutical matrix.

The strain and/or its fermented medium may be selected from one or more lactic bacteria suitable for animal consumption for their ability to display a strong anti-*Helicobacter* bactericidal activity in vitro.

At least one bacterial strain having the above traits and/or its fermented medium may be administered to the pet as a supplement to its normal diet or as a component of a nutritionally complete pet food.

The nutritionally complete pet food composition according to the invention may be in powdered, dried form or a wet, chilled or shelf stable pet food product.

It can also be provided as dietary supplements for pets or pharmaceutical compositions.

The nutritionally complete pet food may be in any suitable form; for example in dried form, semi-moist form and wet form. These pet foods may be produced as is conventional. Apart from the bacteria strains and/or its fermented medium, these pet foods may include any one or more of a starch source, a protein source and lipid source.

Suitable starch sources are, for example, grains and legumes such as corn, rice, wheat, barley, oats, soy, and mixtures of these.

Suitable protein sources may be selected from any suitable animal or vegetable protein source; for example meat and meal, poultry meal, fish meal, soy protein concentrates, milk proteins, gluten, and the like. For elderly animals, it is preferred for the protein source to contain a high quality protein.

Suitable lipid sources include meats, animal fats and vegetable fats.

The choice of the starch, protein and lipid sources will be largely determined by the nutritional needs of the animal, palatability considerations, and the type of product produced. For elderly pets, the pet food preferably contains proportionally less fat than pet foods for younger pets. Further, the starch sources may include one or more of rice, barley, wheat and corn.

Further, various other ingredients, for example, sugar, salt, spices, seasonings, vitamins, minerals, flavouring agents, fats and the like may also be incorporated into the pet food as desired.

For dried pet foods a suitable process is extrusion cooking, although baking and other suitable processes may be used. When extrusion cooked, the dried pet food is usually provided in the form of a kibble. If a prebiotic is used, the prebiotic may be admixed with the other ingredients of the dried pet food prior to processing. A suitable process is described in U.S. Pat. No. 6,197,361, the entire disclosure of which is expressly incorporated herein by reference thereto. If a probiotic microorganism is used, the organism is best coated onto or filled into the dried pet food. A suitable process is described in U.S. Pat. No. 5,968,569, the entire content of which is expressly incorporated herein by reference thereto.

For wet foods, the processes described in U.S. Pat. Nos. 4,781,939 and 5,132,137 may be used to produce simulated meat products. The disclosures of these patents are also expressly incorporated herein by reference thereto. Other procedures for producing chunk type products may also be used; for example cooking in a steam oven. Alternatively, loaf type products may be produced by emulsifying a suitable meat material to produce a meat emulsion, adding a suitable gelling agent, and heating the meat emulsion prior to filling into cans or other containers.

The amount of prebiotic in the pet food is preferably about 20% by weight; and especially about 10% by weight. For example, the prebiotic may comprise about 0.1% to about 5% by weight of the pet food. For pet foods which use chicory as the prebiotic, the chicory may be included to comprise about 0.5% to about 10% by weight of the feed mixture; more preferably about 1% to about 5% by weight.

If a probiotic microorganism is used, the pet food preferably contains about $10^4$ to about $10^{10}$ cells of the probiotic microorganism per gram of the pet food; more preferably about $10^6$ to about $10^8$ cells of the probiotic microorganism per gram. The pet food may contain about 0.5% to about 20% by weight of the mixture of the probiotic microorganism; preferably about 1% to about 6% by weight; for example about 3% to about 6% by weight.

The pet foods may contain other active agents such as long chain fatty acids. Suitable long chain fatty acids include alpha-linoleic acid, gamma linoleic acid, linoleic acid, eicosapentanoic acid, and docosahexanoic acid. Fish oils are a suitable source of eicosapentanoic acids and docosahexanoic acid. Borage oil, blackcurrent seed oil and evening primrose oil are suitable sources of gamma linoleic acid. Safflower oils, sunflower oils, corn oils and soy bean oils are suitable sources of linoleic acid.

If necessary, the pet foods are supplemented with minerals and vitamins so that they are nutritionally complete.

Further, if desired, the bacteria strain may be encapsulated; for example in a sugar matrix, fat matrix or polysaccharide matrix.

The amount of the pet food to be consumed by the pet to obtain a beneficial effect will depend upon the size or the pet, the type of pet, and age of the pet. However an amount of the pet food to provide a daily amount of about $10^3$-$10^{14}$ cfu of at least one lactic acid bacteria strain and/or the equivalent fermentation medium, would usually be adequate. Preferably about $10^9$-$10^{12}$ cfu/day for dogs or $10^7$-$10^{11}$ cfu/day for cats are administered.

The composition according to the invention is particularly intended for the prophylaxis or the treatment of infections related to GHLOs in pets, and in particular in the gastrointestinal tracts or in lower bowel of pets. It is also intended for maintaining healthy digestive function in pets and preventing reinfection by pathogenic strains such as GHLOs. Thus, this composition may also be used as adjuvant of an antibiotherapy against GHLO infestations.

The effect of the composition according to the invention on GHLOs was evaluated by a histologic examination of biopsy sections (see Example 2). If the number of GHLOs per section is no bacteria (grade "0"); less than 5 bacteria (grade "1"); between 5 and 20 bacteria (grade "2") and more than 20 bacteria (grade "3"). This pet food composition is able to decrease GHLO infections in cats and dogs so that the GHLOs load and the urease activity in the fundus are reduced by at least 0.5 grade and by at least 0.5 grade in the antrum.

The effect of the composition on chronic gastritis was also evaluated by cytological examination of biopsy thin sections. The histological classification of chronic gastritis is:

grade 0: superficial fibrosis, 0 neutrophils, 0-10 lymphocytes and plasma cells, no aggregates, normal epithelium;

mild chronic gastritis—grade 1: chronic superficial gastritis, 10-15 lymphocytes or plasma cells involving the superficial interstitial tissue, aggregates<2, normal epithelium, moderate chronic gastritis—grade 2: chronic interstitial gastritis, 10-50 or more lymphocytes or plasma cells involving the full thickness of the micosa, aggregates>3, normal epithelium severe chronic gastritis—grade 3: atrophic gastritis, 10-50 or more lymphocytes or plasma cells, aggregates>3, glandular epithelium changes.

This composition can induce a regression of chronic fundic gastritis, with a median regression of the grade of gastric inflammation of at least about 0.5.

This composition has also been shown to induce a significant reduction of breath odors. Thus, it is intended for treating or preventing secondary disorders related to GHLO infections such as bad breath odors of pets.

Further, the compositions according to the present invention may also be intended for improving longevity of dogs.

EXAMPLES

The following examples are given by way of illustration only and in no way should be construed as limiting the subject matter of the present application. All percentages are given by weight unless otherwise indicated.

Example 1

Selection of Bacterial Strain

In order to select bacterial strain according to the present invention, cultivable GHLOs ($10^7$ bacteria) may be incubated at 37° C. under 5% $CO_2$ for 1-2 hrs in presence of serial dilutions of said bacterial strain growth supernatant (BS) in DMEM. Following incubation, GHLOs-BS mixture is centrifuged at 12,000 g for 3 minutes, the pellet is then washed with 1 ml of 0.9% NaCl, and resuspended in 500 µl of rapid urease test (JATROX®-H.p.-test, Procter&Gamble Pharmaceuticals GmbH, Weiterstadt, Germany). The colorimetric changes, proportional to urease activity, are determined by photometric analysis at an optical density of 550 nm.

Bacterial viability is estimated before and after incubation with LS by plating serial dilutions of GHLOs on serum plates (GC agar, Gibco BRL, Paisley, Scotland) supplemented with 10% horse serum, Inotec, and with 1% Isovitale X (Baltimore Biological Laboratories, Baltimore, Md.), and counting colony forming units (CFU).

Example 2

The effects of a supplement with fermentation medium of *Lactobacillus* on *Helicobacter* spp. infection in dogs is studied.

Materials and Methods

Animals

The ethical committee at the Veterinary School of Lyon—France, approved the study. Nine male beagles, which had naturally contracted a gastric infection with GHLOs, were included in the study. The dogs ranged in weight from 10 to 14 kg and age from 3 to 4 years. The dogs were housed in individual kennels with identical conditions of hygiene and feeding (Veterinary School of Lyon—France). The kennels were cleaned and disinfected daily.

The dogs were regularly fed at 8 a.m. and they had constantly access to water throughout the study. During the whole study, they were fed with a specific diet: VITALITY®—Friskies, France (annexe A).

Experimental Design

Before the treatment, the gastric infection with GHLOs had been confirmed in the 9 beagles by evaluating the identification of GHLOs (histobacteriology), the gastric urease activity (JATROX® test) and the presence of chronic gastritis (histopathology) in fundic and/or antral biopsies of the stomach. All dogs with GHLOs infection were subjected to a treatment for 13 days running. The detection of gastric infection with GHLOs by these tests plus the $^{13}$C-urea breath test was repeated three times: before the treatment [$D_0$], at the end of the treatment [D13] and 30 days after the end of the treatment [$D_{43}$].

Treatment

The treatment was composed by a daily consumption of one acidified milk preparation fermented by *L. johnsonii* NCC 533 for 13 days running. The acidified milk preparation had to be entirely eaten before the specific diet (240 g "VITALITY®/dog).

Evaluation Tests

Clinical examination: during the whole study, the dogs were watched by two veterinary surgeons of the Veterinary School of Lyon—France. The clinical observations had to be recorded in the case report form.

Gastric biopsy: the gastric endoscopy was realised under anaesthesia (ketamine, IMALGENE®, 5 mg/kg—IM). The dogs were fasted for 24 hours. The endoscopy was carried out with a videogastroscope Olympus® GIFK/XV10. At each evaluation day, 12 biopsies had to take from fundus and antrum. Two fundic and antral biopsies had to be immediately used to measure the urease activity of GHLOs. Four fundic and antral biopsies had to had to keep in a "bouin" solution before being used for histobacteriology and histopathology.

Identification of GHLOs (histobacteriology): the identification of GHLOs was made by a histologic examination of biopsy sections. The tissue sections were stained with a Giemsa-type stain and evaluated by light microscopy (×1000). A semi-quantitative evaluation of the GHLOs is done taking into account the localisation in the stomach and the deepness of the extracellular contamination. If the number of GHLOs per section is no bacteria (grade "0"); less than 5 bacteria (grade "1"); between 5 and 20 bacteria (grade "2") and more than 20 bacteria (grade "3"). For each fundic and antral biopsy, two sections were made, then evaluated, and the result was the mean of two evaluations (Ref. Willard M.D. Characterization of naturally developing small intestinal bacterial overgrowth in 16 German Shepherd Dogs. *J Am Vet Med Assoc*, 1994, 204, 1201-1206).

Gastric urease activity (JATROX®—H.P. test, Procter & Gamble, Germany): the principle of the test is that the urea in the test medium is split by the urease present in the GHLOs. The rise in the pH value associated with the splitting of the urea causes a colour change in the indicator medium (phenol red) from yellow to pink/red. The biopsies were tested immediately after their specimen. After the introduction of the biopsy in the indicator medium, the JATROX® a test was read at 180 minutes by a photometer with an ultraviolet detector which was set at 550 nm for reading with a reference at 650 nm. The urease activity in fundic and antral biopsies was the mean of two optical measures.

$^{13}$C-urea breath test: the UBT test was realised two hours after the anaesthesia for endoscopy, so that this one did not influence the results of the UBT. The UBT were made in fasting dogs, without anaesthesia. At a first time, the dogs ate a test meal, which was half of their daily intake; namely 120 g VITALITY®/dog. At a second time, the dogs had an oral administration of 7.5 mg $^{13}$C-urea/dog (MASS TRACE, Woburn—USA). The $^{13}CO_2$ breathed out samples were obtained before the test meal [TB], then 40 minutes after administration of $^{13}$C-urea [T40]. After, the dogs had the second half of their daily food intake. The $^{13}CO_2$ urea breathed out samples were analysed with a gas isotope ratio mass spectrometer (FINNIGAN MAT, Bremen—Germany). To standardise the interlaboratory results, an analogue of international standard for $^{13}$C-reference (Vienna Pee Dee Belemnite or VPDB) was utilised. The atom percent excess for $^{13}CO_2$ was defined as the difference (delta value, δ) in atom percent $^{13}CO_2$ between the baseline sample (sample before test meal and $^{13}$C administration [TB]) and samples obtained after at 40 minutes [T40]× 1000 (44, 45). Results are expressed as an excess δ $^{13}CO_2$ (δ%).

Histopathology (cytology): the histopathology was made by cytoloBT test was made by cytological examination of biopsy thin sections. The impression sections were stained with Hematoxylin-Pholoxin-Saffron (HPS) and observed by microscopy. The criteria for histological diagnoses of gastric biopsies relies on the number of each cell type which is the mean of three fields viewed at ×400 magnification and the amount of lymphocytic aggregates which is the number in a sample at ×200 magnification. The histological classification of chronic gastritis is grade 0: superficial fibrosis, 0 neutrophils, 0-10 lymphocytes and plasma cells, no aggregates, normal epithelium;

mild chronic gastritis—grade 1: chronic superficial gastritis, 10-15 lymphocytes or plasma cells involving the superficial interstitial tissue, aggregates<2, normal epithelium, moderate chronic gastritis—grade 2: chronic interstitial gastritis, 10-50 or more lymphocytes or plasma cells involving the full thickness of the micosa, aggregates>3, normal epithelium severe chronic gastritis—grade 3: atrophic gastritis, 10-50 or more lymphocytes or plasma cells, aggregates>3, glandular epithelium changes (atrophy).

(Ref.: P. Lecoindre, M. Chevallier, R. Gillard and F. Daurin.—Small intestinal bacterial overgrowth and inflammatory bowel diseases in dogs. Evaluation of the therapeutic efficacy of Spiramycine-Metronidazole association. Revue MéD. Vét, 1998; 149:843-852).

Statistical Analysis

Each result of diagnostic tests was the mean of two measures from distinct biopsies. The normality or non-normality of the result distribution had been examined by the Wilk-Shapiro procedure.

The effects of the treatment and post-treatment were evaluated by using a Wilcoxon Signed Rank test (WSRT) and/or Paired t-test.

All statistical calculations were performed with a software program (Statistix®, Excel Microsoft®). A P-value <0.05 was considered as significant.

Results

Kinetic of gastric GHLOs load: The results are presented in Tables 1 and 2.

TABLE 1

Histobacteriology in fundus

| | Fundus/Corps (grade) | | | | | |
|---|---|---|---|---|---|---|
| | $D_0$ | $D_{14}$ | $D_{43}$ | $D_{14}$-$D_0$ | $D_{43}$-$D_{14}$ | $D_{43}$-$D_0$ |
| B01 | 3 | 1 | 2 | −2 | 1 | −1 |
| B02 | 3 | 2 | 3 | −1 | 1 | 0 |
| B04 | 2 | 1 | 0 | −1 | −1 | −2 |
| B05 | 3 | 2 | 1 | −1 | −1 | −2 |
| B06 | 3 | 0 | 3 | −3 | 3 | 0 |
| B07 | 3 | 1 | 2 | −2 | 1 | −1 |
| B08 | 3 | 3 | 2 | 0 | −1 | −1 |
| B09 | 3 | 1 | 1 | −2 | 0 | −2 |
| B10 | 3 | 1 | 3 | −2 | 2 | 0 |
| Median | 3 | 1 | 2 | −2 | 1 | −1 |
| Nbr. < 0 | — | — | — | 8 | 3 | 6 |
| Nbr. = 0 | — | — | — | 1 | 1 | 3 |
| Nbr. > 0 | — | — | — | 0 | 5 | 0 |
| n | 9 | 9 | 9 | 9 | 9 | 9 |
| Mean | 2.9 | 1.3 | 1.9 | −1.6 | 0.6 | −1 |
| +− SEM | 0.11 | 0.29 | 0.35 | 0.29 | 0.47 | 0.29 |

| | $D_{14}$ vs $D_0$ | $D_{43}$ vs $D_{14}$ | $D_{43}$ vs $D_0$ |
|---|---|---|---|
| WSRT | 0.0143 | 0.3270 | 0.0360 |

TABLE 2

Histobacteriology in Antrum

| | Antrum (grade) | | | | | |
|---|---|---|---|---|---|---|
| | $D_0$ | $D_{14}$ | $D_{43}$ | $D_{14}$-$D_0$ | $D_{43}$-$D_{14}$ | $D_{43}$-$D_0$ |
| B01 | 1 | 1 | 2 | 0 | 1 | 1 |
| B02 | 1 | 1 | 2 | 0 | 1 | 1 |
| B04 | 2 | 1 | 0 | −1 | −1 | −2 |
| B05 | 2 | 1 | 2 | −1 | 1 | 0 |
| B06 | 2 | 1 | 1 | −1 | 0 | −1 |
| B07 | 1 | 0 | 1 | −1 | 1 | 0 |
| B08 | 1 | 1 | 1 | 0 | 0 | 0 |
| B09 | 2 | 0 | 2 | −2 | 2 | 0 |
| B10 | 2 | 1 | 1 | −1 | 0 | −1 |
| Median | 2 | 1 | 1 | −1 | 1 | 0 |
| Nbr. < 0 | — | — | — | 6 | 1 | 3 |
| Nbr. = 0 | — | — | — | 3 | 3 | 4 |
| Nbr. > 0 | — | — | — | 0 | 5 | 2 |
| n | 9 | 9 | 9 | 9 | 9 | 9 |
| Mean | 1.6 | 0.8 | 1.3 | −0.8 | 0.6 | −0.2 |
| +− SEM | 0.18 | 0.15 | 0.24 | 0.22 | 0.29 | 0.32 |

| | $D_{14}$ vs $D_0$ | $D_{43}$ vs $D_{14}$ | $D_{43}$ vs $D_0$ |
|---|---|---|---|
| WSRT | 0.0360 | 0.1422 | 0.5896 |

At the end of running of treatment ([$D_0$] to [D14]), the median bacterial load with GHLOs was significantly decreased to grade from "3" to "1" in the fundus (P=0.0143) and from "2" to "1" in the antrum (P=0.0360).

Between the start of treatment and the end of study ([$D_0$] to [D43]), the median bacterial load with GHLOs was significantly decreased to grade from "3" to "2" in fundic biopsies (P<0.0360). In antral biopsies, there is no significantly difference.

Gastric urease activity (JATROX® test): The results are presented in Tables 3 and 4.

TABLE 3

Gastric urease activity (JATROX ® test) in fundus

| | Fundus/Corps (optical density) | | | | | |
|---|---|---|---|---|---|---|
| | $D_0$ | $D_{14}$ | $D_{43}$ | $D_{14}$-$D_0$ | $D_{43}$-$D_{14}$ | $D_{43}$-$D_0$ |
| B01 | 0.43 | 0.34 | 0.43 | −0.09 | 0.09 | 0.01 |
| B02 | 0.42 | 0.39 | 0.44 | −0.04 | 0.05 | 0.01 |
| B04 | 0.54 | 0.00 | 0.44 | −0.53 | 0.44 | −0.10 |
| B05 | 0.47 | 0.31 | 0.49 | −0.16 | 0.18 | 0.02 |
| B06 | 0.44 | 0.42 | 0.43 | −0.02 | 0.01 | −0.01 |
| B07 | 0.52 | 0.40 | 0.41 | −0.11 | 0.01 | −0.11 |
| B08 | 0.68 | 0.31 | 0.40 | −0.37 | 0.09 | −0.28 |
| B09 | 0.45 | 0.35 | 0.38 | −0.10 | 0.02 | −0.08 |
| B10 | 0.44 | 0.32 | 0.43 | −0.13 | 0.01 | −0.01 |
| Median | 0.46 | 0.34 | 0.43 | −0.12 | 0.09 | −0.01 |
| Nbr. < 0 | — | — | — | 9 | 0 | 6 |
| Nbr. = 0 | — | — | — | 0 | 0 | 0 |
| Nbr. > 0 | — | — | — | 0 | 9 | 3 |
| n | 9 | 9 | 9 | 9 | 9 | 9 |
| Mean | 0.49 | 0.32 | 0.43 | −0.17 | 0.11 | −0.06 |
| +− SEM | 0.03 | 0.04 | 0.01 | 0.06 | 0.04 | 0.03 |

| | $D_{14}$ vs $D_0$ | $D_{43}$ vs $D_{14}$ | $D_{43}$ vs $D_0$ |
|---|---|---|---|
| Paired t-test | 0.0155 | 0.0381 | 0.0921 |

TABLE 4

Gastric urease activity (JATROX ® test) in Antrum

| | Antrum (optical density) | | | | | |
|---|---|---|---|---|---|---|
| | $D_0$ | $D_{14}$ | $D_{43}$ | $D_{14}$-$D_0$ | $D_{43}$-$D_{14}$ | $D_{43}$-$D_0$ |
| B01 | 0.31 | 0.00 | 0.00 | −0.31 | 0.00 | −0.31 |
| B02 | 0.33 | 0.05 | 0.00 | −0.28 | −0.05 | −0.33 |
| B04 | 0.41 | 0.00 | 0.00 | −0.41 | 0.00 | −0.41 |
| B05 | 0.46 | 0.00 | 0.00 | −0.46 | 0.00 | −0.46 |
| B06 | 0.28 | 0.00 | 0.00 | −0.28 | 0.00 | −0.28 |
| B07 | 0.00 | 0.00 | 0.00 | −0.02 | 0.00 | 0.00 |
| B08 | 0.00 | 0.07 | 0.00 | 0.07 | −0.07 | 0.00 |
| B09 | 0.05 | 0.00 | 0.00 | −0.05 | 0.00 | −0.05 |
| B10 | 0.00 | 0.00 | 0.00 | 0.00 | 0.00 | 0.00 |
| Median | 0.28 | 0.00 | 0.00 | −0.28 | 0.00 | −0.28 |
| Nbr. < 0 | — | — | — | 6 | 2 | 6 |
| Nbr. = 0 | — | — | — | 2 | 7 | 3 |
| Nbr. > 0 | — | — | — | 1 | 0 | 0 |
| n | 9 | 9 | 9 | 9 | 9 | 9 |
| Mean | 0.20 | 0.01 | 0.00 | −0.19 | −0.01 | −0.20 |
| +− SEM | 0.06 | 0.01 | 0.00 | 0.07 | 0.01 | 0.06 |

| | $D_{14}$ vs $D_0$ | $D_{43}$ vs $D_{14}$ | $D_{43}$ vs $D_0$ |
|---|---|---|---|
| Paired t-test | 0.0197 | 0.1756 | 0.0123 |

At the end of the running of treatment ($[D_0]$ to $[D_{14}]$), the mean of urease activity decreased significantly of 35% in fundus (P=0.0155) and 93% in antrum (P=0.0197).

Twenty-nine days after the end of treatment ($[D_{14}]$ to $[D_{43}]$), the mean urease activity increased significantly of 35% in fundic biopsies (P=0.0381) but still remained lower than at the beginning of the treatment. The antral urease activity was not modified and stayed null.

Global urease activity ($^{13}C$-urea breath test):

The results are given in Table 5.

TABLE 5

Global urease activity ($^{13}C$-urea breath test)

| | $D_0$ | $D_{14}$ | $D_{43}$ | $D_{14}$-$D_0$ | $D_{43}$-$D_{14}$ | $D_{43}$-$D_0$ |
|---|---|---|---|---|---|---|
| B01 | 34 | 6 | 55 | −28 | 49 | 21 |
| B02 | 18 | 26 | 21 | 8 | −5 | 3 |
| B04 | 165 | 24 | 50 | −141 | 26 | −116 |
| B05 | 15 | 7 | 6 | −8 | −1 | −9 |
| B06 | 18 | 20 | 19 | 2 | −1 | 1 |
| B07 | 12 | 13 | 22 | 1 | 9 | 10 |
| B08 | 47 | 17 | 15 | −30 | −2 | −32 |
| B09 | 20 | 10 | 9 | −10 | −1 | −11 |
| B10 | 32 | 9 | 13 | −23 | 4 | −19 |
| Median | 20 | 13 | 20 | −10 | −1 | −9 |
| Nbr. < 0 | — | — | — | 6 | 5 | 5 |
| Nbr. = 0 | — | — | — | 0 | 0 | 0 |
| Nbr. > 0 | — | — | — | 3 | 4 | 4 |
| n | 9 | 9 | 9 | 9 | 9 | 9 |
| Mean | 40 | 14 | 23 | −26 | 9 | −17 |
| +− SEM | 16 | 3 | 6 | 15 | 6 | 13 |

| | $D_{14}$ vs $D_0$ | $D_{43}$ vs $D_{14}$ | $D_{43}$ vs $D_0$ |
|---|---|---|---|
| WSRT | 0.0494 | 0.4772 | 0.3433 |

Between the start and the end of the treatment ($[D_0]$ to $[D_{14}]$), the median $^{13}C$-enrichment of 35% $^{13}CO_2$-breathed out decreased significantly (P=0.049).

At the end of 29 days after the end of treatment ($[D_{14}]$ to $[D_{43}]$), the $^{13}C$-enrichment of $^{13}CO_2$-breathed out was not significantly modified.

Chronic gastritis ($^{13}C$-urea breath test):

The results are given in Tables 6 and 7.

TABLE 6

Histopathology in fundus

| | Fundus/Corps (grade) | | | | | |
|---|---|---|---|---|---|---|
| | Inclusion | $D_{14}$ | $D_{43}$ | $D_{14}$-Incl. | $D_{43}$-$D_{14}$ | $D_{43}$-Incl. |
| B01 | 2 | 1 | 0 | −1 | −1 | −2 |
| B02 | 1 | 0 | 0 | −1 | 0 | −1 |
| B04 | 2 | 0 | 0 | −2 | 0 | −2 |
| B05 | 1 | 1 | 1 | 0 | 0 | 0 |
| B06 | 1 | 0 | 1 | −1 | 1 | 0 |
| B07 | 1 | 0 | 0 | −1 | 0 | −1 |
| B08 | 1 | 0 | 0 | −1 | 0 | −1 |
| B09 | 1 | 0 | 0 | −1 | 0 | −1 |
| B10 | 2 | 0 | 0 | −2 | 0 | −2 |
| Median | 1 | 0 | 0 | −1 | 0 | −1 |
| Nbr. < 0 | — | — | — | 8 | 1 | 7 |
| Nbr. = 0 | — | — | — | 1 | 7 | 2 |
| Nbr. > 0 | — | — | — | 0 | 1 | 0 |
| N | 9 | 9 | 9 | 9 | 9 | 9 |
| Mean | 1.3 | 0.2 | 0.2 | −1.1 | 0.0 | −1.1 |
| +− SEM | 0.17 | 0.15 | 0.15 | 0.20 | 0.17 | 0.26 |

| | $D_{14}$-Incl. | $D_{43}$-$D_{14}$ | $D_{43}$-Incl. |
|---|---|---|---|
| WSRT | 0.0143 | 0.7500 | 0.0225 |

TABLE 7

Histopathology in antrum

| | Antrum (grade) | | | | | |
|---|---|---|---|---|---|---|
| | Inclusion | $D_{14}$ | $D_{43}$ | $D_{14}$-Incl. | $D_{43}$-$D_{14}$ | $D_{43}$-Incl. |
| B01 | 1 | 2 | 0 | 1 | −2 | −1 |
| B02 | 1 | 0 | 2 | −1 | 2 | 1 |
| B04 | 0 | 0 | 0 | 0 | 0 | 0 |
| B05 | 0 | 1 | 1 | 1 | 0 | 1 |
| B06 | 1 | 0 | 1 | −1 | 1 | 0 |
| B07 | 1 | 0 | 1 | −1 | 1 | 0 |
| B08 | 1 | 1 | 1 | 0 | 0 | 0 |
| B09 | 1 | 0 | 0 | −1 | 0 | −1 |
| B10 | 1 | 1 | 0 | 0 | −1 | −1 |
| Median | 1 | 0 | 1 | 0 | 0 | 0 |
| Nbr. < 0 | — | — | — | 4 | 2 | 3 |
| Nbr. = 0 | — | — | — | 3 | 4 | 4 |
| Nbr. > 0 | — | — | — | 2 | 3 | 2 |
| n | 9 | 9 | 9 | 9 | 9 | 9 |
| Mean | 0.8 | 0.6 | 0.7 | −0.2 | 0.1 | −0.1 |
| +− SEM | 0.15 | 0.24 | 0.24 | 0.28 | 0.39 | 0.26 |

| | $D_{14}$-Incl. | $D_{43}$-$D_{14}$ | $D_{43}$-Incl. |
|---|---|---|---|
| WSRD | 0.5294 | 0.8336 | 0.7874 |

At the end of running of treatment ([Incl.] to [D14]), the median chronic gastritis was significantly decreased to grade from "1" to "0" in the fundus (P=0.0143). This decrease was maintained until the end of the study. Any significant modification of median grade had not showed in antral biopsies.

Conclusions

| | TREATMENT | | POST-TREATMENT | |
|---|---|---|---|---|
| | FUNDUS | ANTRUM | FUNDUS | ANTRUM |
| | ([D$_{14}$] vs [D$_0$])<br>Specific diet +<br>*L. johnsonii* NCC 533<br>fermented milk preparation | | ([D$_{43}$] vs [D14])<br>Specific diet | |
| GHLOs [(2)-a] | (−)* | (−)* | ns | ns |
| Urease Activity [(1)-b] | (−)* | (−)* | (+)* | ns |
| Urease Activity [(2)-c] | | (−)* | ns | |
| | ([D$_{14}$] vs Inclusion) | | ([D$_{43}$] vs [D$_{14}$]) | |
| Chronic<br>Gastritis [(2)-d] | (−)* | ns | ns | ns |

[(1)] Paired t-test;
[(2)] Wilcoxon Signed Rank test - (−) (+) negative or positive variation - P < 0.05 - [a] Histobacteriology - [b] JATROX ® test - [c13] C-Urea Breath test - [d] Histopathology In dogs having a gastric GHLOs infection with a chronic gastritis, the consumption of an acidified milk preparation fermented by *L. johnsonii* NCC 533 was able to obtain:

in fundus and in antrum, a significant decrease of GHLOs load and the urease activity and the regression of chronic gastritis during the treatment, in fundus, a significant regression of chronic gastritis that was maintained after the end of treatment, no side effect.

Example 3

Anti-*Helicobacter* Properties Present in the Culture Supernatants of Different Lactobacilli Strains The in-vitro anti-GHLO properties of growth culture supernatants of Lactobacilli of the isolated strains: NCC 533, NCC 2583 and NCC 2628 were assessed by inhibition of urease activity.

*H. bizzozzeronii* and *H. salomonis* were grown in Columbia agar—5% sheep blood. *H. felis* was grown on brain heart infusion (BHI) agar containing 3 g/L yeast extract and 10% sheep blood. All *Helicobacter* species were maintained in a microaerophilic atmosphere (85% $N_2$/10% $CO_2$/5% $O_2$) at 37° C. for 48 h. Bacteria were harvested in BHI broth supplemented with 2.5 g/L yeast extract. The number of bacteria was estimated by measuring the optical density at 600 nm (1 OD600=$10^8$ bacteria/ml).

Culture supernatants, pure or pre-diluted in the appropriated medium, were finally diluted 1:2 in DMEM medium. After adjusting pH to 4.2, samples were sterilized by filtration through 0.2 μM. The equivalent of $1\times10^7$ *H. pylori* was added to tubes containing 500 μl of different samples and tubes were further maintained for 1 hr at 37° C. in a cell incubator (5% $CO_2$). Bacteria were harvested by centrifugation. Bacterial pellets were washed once in 0.9% NaCl and resuspended in 250 μl of urease test reagent (JATROX®-H.p.-test; Procter & Gamble Pharmaceutical). After an additional incubation of 1 h at 37° C., the colorimetric changes, proportional to urease activity, were determined by spectrophotometry at an optical density (OD) of 550 nm.

Fermented Supernatant Preparation

The Lactobacilli from Nestle culture collection named NCC 2583 and NCC 2628 were grown in MRS-Pasteur medium. *E. faecium* SF68 and *S. boulardii* SB20 were grown in HJL and YPF medium, respectively. After 48 h at 37° C., bacteria were pelleted and fermented supernatants were recovered and kept frozen at −20° C. until further use.

Results

Stocks of *Lactobacillus* strains, NCC 2583 and NCC 2628, of *E. faecium* SF68 (Bioferment) and of *S. boulardii* SB20 (Levucell) were grown in parallel in their appropriated media. The different fermented supernatants were tested for their inhibitory capacity against *H. bizzozzeronii*, *H. salominis* and *H. felis* using the urease test. A NCC 533 growth culture supernatant was used as a positive control and the culture media alone were used as negative controls in the assays.

Table 8 shows the results of two separate experiments. The fermented (supernatant of the *L. acidophilus* NCC 2628 totally inhibited the urease activity of *H. bizzozzeronii*, *H. salominis* and *H. felis*. The fermented supernatant of *L. rhiamnosus* NCC 2583 partially inhibited the urease activity of *H. bizzozzeronii* and *H. salomonis* but not that of *H. felis*.

The incubation of any of the *Helicobacter* species with the *L. jonhsonii* NCC 533 culture supernatant led to a complete inhibition of their urease activity. No inhibition of urease activity was observed when incubating the three *Helicobacter* species with the growth culture supernatants of *E. faecium* SF68, of *S. boulardii* SB20.

TABLE 8

Effect of different fermented supernatants on GHLO urease activity

| | | | Urease activity (OD$_{550\,nm}$) | | |
|---|---|---|---|---|---|
| Sample | Species | Initial pH | *H. bizzozzeronii* | *H. felis* | *H. salomonis* |
| MRS-Pasteur | — | 6.6 | 0.5 | 0.5 | 0.5 |
| YPD | — | 6.4 | 0.5 | 0.6 | 0.5 |
| CNCM I-1225 | *L. johnsonii* | 3.9 | 0.0<br>0.0 | 0.0<br>0.0 | 0.0<br>0.0 |
| CNCM I-2583 | *L. rhamnosus* | 4.1 | 0.3 | 0.2 | 0.5 |
| CNCM I-2628 | *L. acidophilus* | 4.1 | 0.0 | 0.0 | 0.0 |
| SF68 | *E. faecium* | 5.1 | 0.5 | 0.5 | 0.5 |
| SB20 | *S. boulardii* | 4.2 | 0.5 | 0.5 | 0.6 |

3 Lactobacilli, *E. faecium, S. boulardii* were cultured for 48 h in their appropriated media. Dilution ½ of the fermented culture supernatants were incubated with 2×107 bacteria/ml. After incubation of 1 h, the urease activities of *H. bizzozzeronii, H. felis* and *H. salomonis* were assessed by spectrophotometry. Total inhibition $OD_{550nm}=0$; No inhibition $OD_{550nm}>0.5$.

Example 4

Dry Dog Food

A feed mixture is made up of about 58% by weight corn, about 5.5% by weight of corn gluten, about 22% by weight of chicken meal, 2.5% dried chicory, fermented milk by strains of *Lactobacillus johnsonii* NCC 533 (CNCM-I 1225) and *Lactobacillus paracasei* (CNCM-I 2116) so that the corresponding amount for the dog is about $10^9$-$10^{12}$ cfu/day, and salts, vitamins and minerals making up the remainder.

The fed mixture is fed into a preconditioner and moistened. The moistened feed is then fed into an extruder-cooker and gelatinized. The gelatinized matrix leaving the extruder is forced through a die and extruded. The extrudate is cut into pieces suitable for feeding to dogs, dried at about 110° C. for about 20 minutes, and cooled to form pellets.

This dry dog food is able to improve pet health, and particularly prevents disorders related to GHLOs infection in pets.

Example 5

A trial is conducted on a panel of 20 male beagles, which had naturally contracted a gastric infection with GHLOs. All dogs were first given an antibiotics a classical treatment for eradication of GHLOs, comprising administering two different antibiotics (Spiramycine and Metronidazole) and one antisecretory like Omeprazole during 1 week.

After 7 days of treatment, half the dogs were GHLOs negative, i.e. no *Helicobacter* organisms were detected by histobacteriology, no gastric urease activity and a $^{13}$C-Urea Breath test value lower than 5% of increase over baseline at 40 minutes.

After the treatment, half of the dogs were fed with Friskies Menu Energy product, which is dried dog food available on the market, as a control food. The 10 remaining dogs were fed with a test food corresponding to the Friskies Menu Energy product except that it contains pellets of dry fermented milk by strains of *Lactobacillus johnsonii* NCC 533 (CNCM-I 1225) and *Lactobacillus paracasei* (CNCM-I 2116), so that the amount for a dog is of about $10^9$-$10^{12}$ cfu/day.

The $^{13}$C-Urea Breath test and *Helicobacter* detection by histobacteriology were measured again 6 weeks after feeding these two different diets. The result shows that 20% of the dogs fed with normal Friskies Menu Energy product, became positive in 6 weeks. All dogs fed with the test food were negative after 6 weeks.

This composition is efficient as an adjuvant in antibiotherapies for GHLOs reinfestation prevention.

Example 6

Canned Pet Food

A mixture is prepared from 73% of poultry carcass, pig lungs and beef liver (ground), 16% of wheat flour, 2% of dyes and 9% of fermented milk by strains of *Lactobacillus johnsonii* NCC 533 (CNCM-I 1225) and *Bifidobacterium lactis* (ATCC 27536), vitamins, and inorganic salts. This mixture is emulsified at 12° C. and extruded in the form of a pudding which is then cooked at a temperature of 90° C. It is cooled to 30° C. and cut in chunks. 45% of these chunks are mixed with 55% of a sauce prepared from 98% of water, 1% of dye and 1% of guar gum. Tinplate cans are filled and sterilized at 125° C. for 40 min.

This wet composition is intended for preventing or treating disorders related to GHLO infections in pets.

Example 7

Effect on Bad Breath Odors 10 dogs with GHLOs in stomach were fed with the same diet that in example 2 for 2 weeks. The breath odor was measured in each dogs at the beginning and at the end of the treatment by the help of an halitometer.

This experiment showed that feeding the dogs with a composition containing an acidified milk preparation fermented by *L. johnsonii* NCC 533 induces an significant reduction of breath odors.

Furthermore there was clear correlation between the level of infection by *Helicobacter* and the breath odors.

What is claimed is:

1. A pet-treatment formulation for treatment of non-*Helicobacter pylori*, gastric *Helicobacter*-like organism disorders in pets comprising a protein source, a starch source, a lipid source and a strain of lactic acid bacteria selected from the group consisting of *Lactobacillus reuteri, Lactobacillus paracasei, Lactobacillus ruminis, Lactobacillus rhamnosus, Lactobacillus fermentum, Bifidobacterium* sp., *Bifidobacterium lactis, Bifidobacterium animalis*, and combinations thereof, wherein the lactic acid bacteria is present in an amount of $10^9$ to $10^{12}$ cfu for the treatment of non-*Helicobacter pylori*, gastric *Helicobacter*-like organism disorders in pets, and wherein the formulation does not include another genus of lactic acid bacteria, said lactic acid bacteria having been isolated and selected for its ability to display an anti-*Helicobacter* bactericidal activity in vitro, wherein the starch source is selected from the group consisting of grains, legumes, corn, rice, wheat, barley, oats, soy and mixtures thereof.

2. A pet food composition for treatment of non-*Helicobacter pylori*, gastric *Helicobacter*-like organism (GHLO) disorders in pets and containing an isolated strain of lactic acid bacteria selected from the group consisting of *Lactobacillus reuteri, Lactobacillus paracasei, Lactobacillus ruminis, Lactobacillus rhamnosus, Lactobacillus fermentum, Bifidobacterium* sp., *Bifidobacterium lactis, Bifidobacterium animalis*, and combinations thereof, wherein the lactic acid bacteria is present in an amount of $10^9$ to $10^{12}$ cfu, and wherein the composition does not include another genus of lactic acid bacteria, said lactic acid bacteria being isolated and selected for its ability to display an anti-*Helicobacter* bactericidal activity in vitro for the treatment of non-*Helicobacter pylori*, gastric *Helicobacter*-like organism disorders in pets, wherein the pet food composition comprises an ingestible support and a starch source selected from the group consisting of grains, legumes, corn, rice, wheat, barley, oats, soy and mixtures thereof.

* * * * *